United States Patent
Cooley et al.

(10) Patent No.: US 6,909,251 B2
(45) Date of Patent: Jun. 21, 2005

(54) MEDICAL NEEDLE REMOVAL DEVICE

(76) Inventors: Stephen Francis Gerard Cooley, 9 Meadow View, Adderbury, Banbury, Oxfordshire, OX17 3LZ (GB); Philip William Field, 10 Colesbourne Road, Bloxham, Banbury, Oxfordshire, OX15 4TB (GB)

(*) Notice: Subject to any disclaimer, the term of this patent is extended or adjusted under 35 U.S.C. 154(b) by 0 days.

(21) Appl. No.: 10/745,202
(22) Filed: Dec. 22, 2003

(65) Prior Publication Data
US 2005/0012478 A1 Jan. 20, 2005

(51) Int. Cl.[7] .............................. H02P 5/00
(52) U.S. Cl. .................. 318/139; 318/445; 318/466
(58) Field of Search ................. 318/139, 445, 318/466; 604/187; 424/489

(56) References Cited
U.S. PATENT DOCUMENTS

2003/0040715 A1 * 2/2003 D'Antonio et al. ......... 604/187
2003/0054044 A1 * 3/2003 Potter et al. ................ 424/489

* cited by examiner

Primary Examiner—Karen Masih
(74) Attorney, Agent, or Firm—Paul E Milliken; Ray L Weber

(57) ABSTRACT

Apparatus (10) for the removal of a needle assembly A having a needle hub H which is screw-threadedly engaged with a syringe S, said apparatus (10) comprising a housing (11) having an opening (16) for insertion of the needle assembly A and adjacent portion of the syringe, a socket (19) mounted within the housing (11) in alignment with the opening (16) with a cavity (22) shaped to receive the hub H and a coaxial through-bore (23) to accommodate the needle. The socket (19) holds the hub rotationally fast allowing the syringe S and needle assembly A to be unscrewed, and an ejector means (51) located in the housing ejects the unscrewed needle assembly A from the socket (19) into a collection container (42) located within the housing (11).

11 Claims, 2 Drawing Sheets

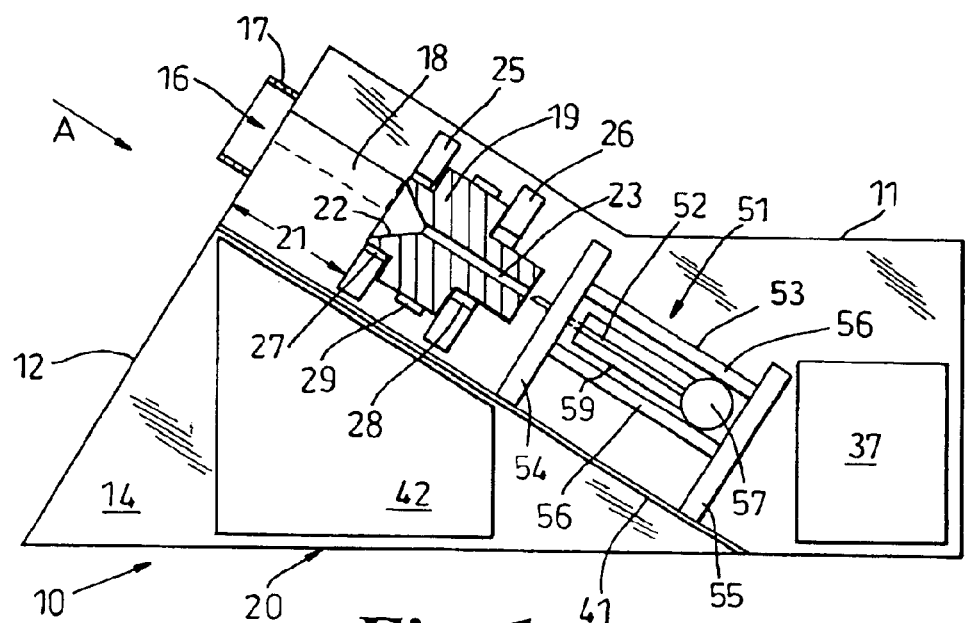
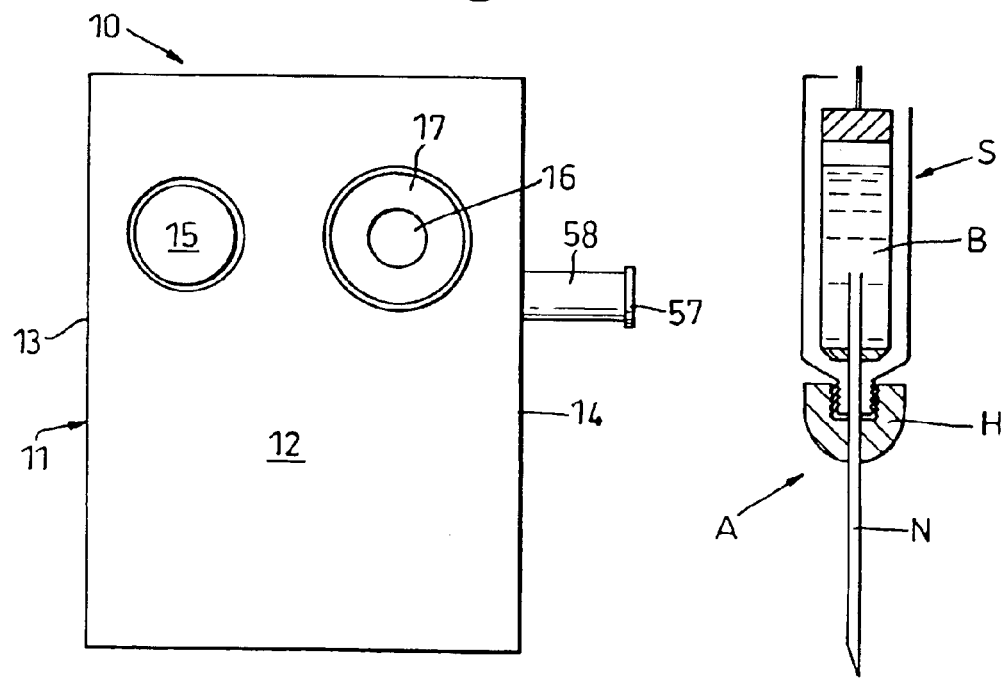

MEDICAL NEEDLE REMOVAL DEVICE

FIELD

This invention is a means of safely removing used needles from the body of a multi-use syringe without the need to undo and remove the needle manually.

BACKGROUND OF THE INVENTION

Multi-use syringes are used in medicine, veterinary practice and especially in dentistry for the administration of anaesthetic injections into the mouth, or may be used for mass-vaccination programs. Devices are known for the removal of used disposable needles from the syringe. Typically a needle disposal container may be provided with a lid having a shaped aperture for engagement with a needle hub. The technician or nurse carefully inserts the needle into the aperture so that the needle hub is held stationary within the aperture and then unscrews the syringe from the needle hub and the needle drops into the disposal container.

In another known apparatus shown in U.S. Pat. No. 5,531,323, there is disclosed a disposal container fitted with a motorized device that facilitates one handed needle removal. The devices disclosed in '323 for engaging the needle hub are all provided on the lid of a disposal container and frictionally engage the side of an inserted needle hub causing the hub to unscrew. This allows the needle to fall freely into the container after removal. However, if the frictional engagement is insufficient to unscrew the needle hub then the needle will remain in place. A more positive unscrewing action is shown in '323 provided by an open aperture in a rotatable gear wheel which engages the external surface of the hub. However in order to prevent the hub from passing completely through the aperture provision must be made for the syringe body to act as a stop when inserting the needle hub into the aperture so that the needle and hub are not fully enclosed within the disposal container when the needle hub is unscrewed. This may give rise to difficulties in use and also to problems of cross contamination and infection.

The present invention provides a needle removal device in which the needle and hub and adjacent syringe body are all located within a housing when the needle is unscrewed thereby reducing the chances of cross contamination and danger of infection or injury to the operator removing the needle.

STATEMENTS OF INVENTION

According to the present invention there is provided apparatus for the removal of a needle assembly having a needle hub which is screw-threadedly engaged with a syringe, said apparatus comprising a housing having an opening for insertion of the needle assembly and adjacent portion of the syringe, a socket mounted within the body in alignment with the opening, said socket having a cavity internally shaped to receive the hub and a coaxial through-bore to accommodate the needle, the socket holding the hub rotationally fast relative thereto allowing the syringe to be unscrewed from the needle assembly, and an ejector means located in the housing for ejecting the unscrewed needle assembly from the socket into a collection container located within the body.

The term syringe covers both syringes with disposable cylindrical bodies and multi-use re-fillable syringes.

Preferably, the socket is rotatable by a motor to unscrew a needle hub when the syringe is held stationary relative to the housing. The motor may be of any suitable type but is preferably an electrical D.C. motor which rotates the socket through a gear train. The motor is preferably a 12V motor which is driven by at least one battery located within the housing. The batteries may be rechargeable.

The motor is operated by a manual switch located externally of the housing.

The container may be removable from the housing for disposal of needle assemblies collected therein, in which case the container is preferably secured in the housing by a key operated lock thereby preventing unauthorised or accidental removal from the housing.

The ejector means comprises a reciprocable pin which is arranged coaxially with the through-bore in the socket and is a sliding fit therein to push any needle out of the bore. The pin is slidably mounted in a support frame and is moveable by a handle located externally of the housing.

The housing, or at least a portion thereof, may be made from an optically transparent material, e.g a transparent plastic material e.g perspex, PET, polycarbonate, to permit confirmation that a needle assembly has been removed before withdrawing a syringe from the housing.

DESCRIPTION OF DRAWINGS

The invention will be described by way of example and with reference to the accompanying drawings in which:

FIG. 1 is a first side elevation of apparatus according to the present invention, FIG. 2 is a front elevation of the apparatus of FIG. 1 taken in the direction of arrow A, FIG. 5 shows a typical conventional syringe and needle assembly.

DETAILED DESCRIPTION OF THE INVENTION

Figure 3:
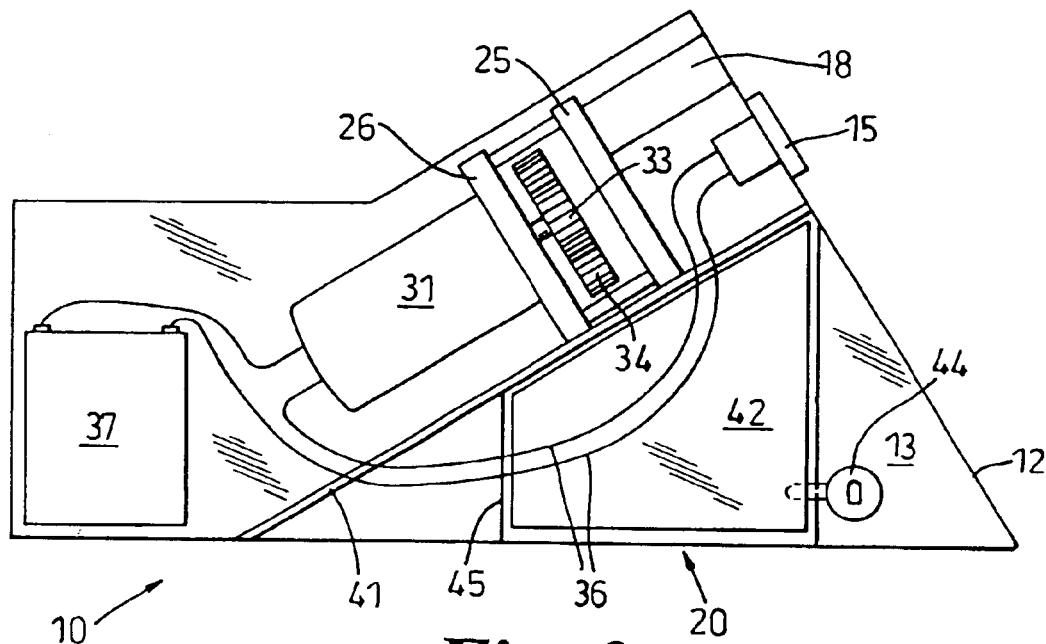
FIG. 3 is a second side elevation taken from the other side of the apparatus to FIG. 1.

With reference to FIG. 5, there is shown a typical medical syringe S having a needle assembly A screwed onto the barrel B of the syringe. The needle assembly comprises needle N which is mounted within a hub H which screws into the barrel B. Disposable needle assemblies A are removable from the barrel by gripping or holding the external surface of the hub H and unscrewing.

With reference to FIGS. 1–4, there is shown apparatus 10 for the removal of screw-on needle assembly A from the barrel B of a re-usable syringe S used for medical, dental or veterinary purposes.

The apparatus comprises a hollow housing 11 having a front panel 12 inclined to its base 20 and side panels 13 & 14. The side panels 13 & 14 are made from a transparent plastics material allowing the inside of the apparatus to be viewed from outside. An electrical on/off switch 15 is mounted on the front panel 12 and an opening 16 is provided in the front panel for insertion of a syringe and needle assembly into the apparatus. The opening 16 may be surrounded by outer guide 17 mounted externally of the front panel 12 and an inner guide 18 mounted internally of the front panel 12. The inner guide 18 is arcuate in cross-section and in use bears only against the upper surface of any syringe barrel inserted into the opening 16.

A generally cylindrical socket 19 is located within the housing 11 aligned with the opening 16 but set back therefrom. The socket 19 is set back from the opening 16 by a gap 21 just greater than the length of the needle assembly to unscrewed, this gap 21 being bridged by the inner guide 18. The socket 19 has a cavity 22 whose mouth is directed towards the opening with a through-bore 23 extending from the base of the cavity to the other end of the socket.

The socket 19 is rotatabley mounted between a pair of spaced plates 25 & 26 and rotates within respective bearing bushes 27 28 located in the plates. A coaxial gear form 29 may be integrally formed on the outer surface of the socket 19, or alternatively a separate gear wheel may be assembled to the socket 19.

An electric motor 31 is mounted to the back side of the rear plate 26 to one side of the socket 19. The motor shaft 32 extends through the plate 26 and is fast with a gear wheel 33 located on the other side of the plate 26 and which is aligned with the gear form 29 on the socket 19. The gear wheel 33 is drivably connected to the socket 19 via a gear train containing at least one reduction gear wheel 34. The motor is a 12 volt DC motor which is electrically connected to the switch 15 by cables 36 and is powered by a 12 volt battery 37 located at the rear of the housing 11. The switch 15 may include a timer device to switch off the motor automatically after a predetermined time limit. The battery 37 may be a rechargeable battery and alternatively or additionally the apparatus may include a rectifier and voltage reducer for connection to a AC power source.

The plates 25 & 26 are mounted on a support plate 41 substantially normal thereto. The support plate 21 is secured in the housing and is inclined relative to the base 20 of the housing substantially normal to the front panel 12. The support plate 41 divides the housing 19 into upper and lower portions with a collection container 42 located in the lower portion below the socket 19. An aperture 43 in the front portion of the plate 41 allows removed needle assemblies to fall into the container 42. The container 42 is removable through an aperture 45 in the side panel 13 and may be locked in-situ within the housing 11 by a key operated lock 44.

Also mounted on the support plate 41 is an ejector means 51 for ejecting removed needle assemblies from the socket 19. The ejector means has an ejector pin 52 reciprocably mounted in a support frame 53 coaxially with the through-bore. 23 in the socket 19. The frame 53 comprises a pair of spaced apart plates 54 & 55 linked by struts 56. The plates 54 & 55 are fixed to the support plate 41 and pin 52 is guided for movement relative to the plates 54, 55 by guide bushes located in the plates 54 & 55. The pin 52 is slidable within the through-bore 23 and is operated manually by a handle 57 located externally of the housing 11. The handle 57 is connected to the ejector pin 52 by a link 58 and the reciprocating movement of the pin is accommodated by a slot 59 in the side panel 14.

Figure 4:
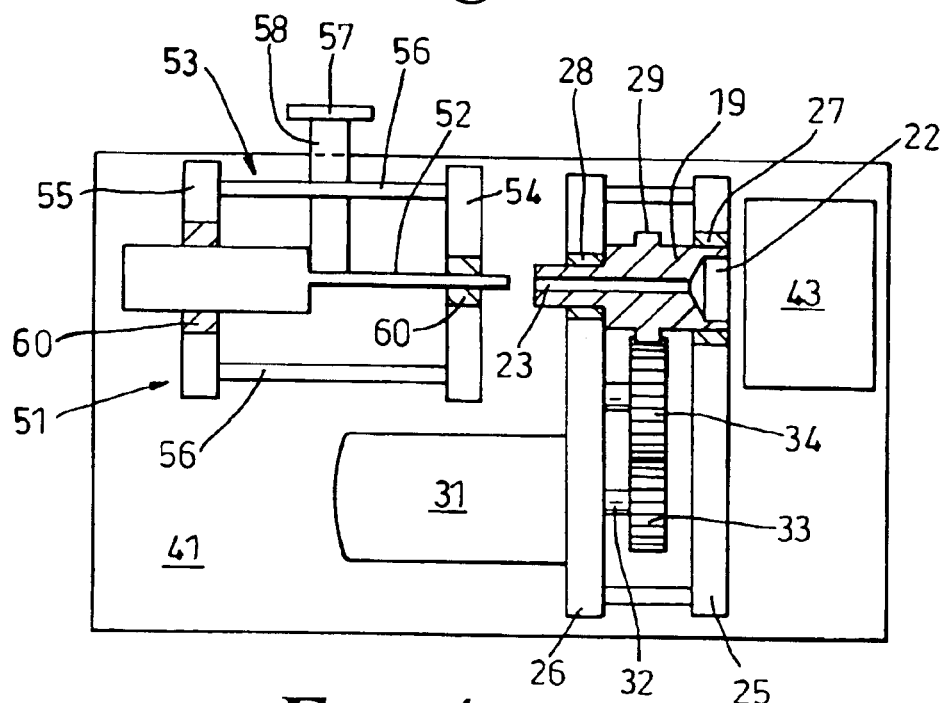
FIG. 4 is view from above showing the layout of the socket, motor, gears, and ejector means on the support plate.

The layout of the socket, ejector means and motor is shown in FIG. 4.

A needle assembly A and the adjacent front portion of a syringe S is inserted through the opening 16 in the housing 11 and is guided by the inner and outer guides 17 & 18 so that the needle assembly A passes into the cavity 22 of the socket 19. The internal form of the cavity 19 is such as to hold the needle hub H against rotation relative thereto and the through-bore 23 accommodates the needle N.

The needle assembly A is unscrewed by activating the motor 31 via switch 15 and holding the syringe against rotation. The socket unscrews the hub H and after removal of the syringe the needle assembly is ejected from the cavity 22 and through-bore 23 by operation of the ejector means 51 to sweep the bore 23 empty. The ejected needle assembly A falls through aperture 43 and is collected in the container 42. When a container is full is can be removed for disposal of the needle assemblies.

It can be seen that the needle assemblies can be removed from the syringes and disposed of without any contact from a technician, nurse or other operator.

What is claimed is:

1. Apparatus for the removal of a needle assembly having a needle hub which is screw-threadedly engaged with a syringe, said apparatus comprising a housing having an opening for insertion of the needle assembly and adjacent portion of the syringe, a socket mounted within the body in alignment with the opening, said socket having a cavity internally shaped to receive the hub and a coaxial through bore to accommodate the needle, the socket cavity holding the hub rotationally fast relative thereto allowing the syringe to be unscrewed from the needle assembly, and an ejector means located in the housing for ejecting the unscrewed needle assembly from the socket into a collection container located within the housing.

2. Apparatus as claimed in claim 1 wherein the socket is rotatable by a motor to unscrew a needle hub when the syringe is held stationary relative to the housing.

3. Apparatus as claimed in claim 2, wherein the motor is a electrical D.C. motor which rotates the socket through a gear train.

4. Apparatus as claimed in claim 3 wherein the motor is driven by a battery located within the housing.

5. Apparatus as claimed in claim 4 wherein the motor is, operated through a manual switch located externally of the housing.

6. Apparatus as claimed in any claim 1, wherein the container is removable from the housing for disposal of needle assemblies collected therein.

7. Apparatus as claimed in claim 6 wherein the container is secured in the housing by a key operated lock thereby preventing unauthorised or accidental removal from the housing.

8. Apparatus as claimed in claim 1 wherein the ejector means comprises a reciprocable pin which is arranged coaxially with the through-bore and is a sliding fit therein.

9. Apparatus as claimed in claim 8 wherein the pin is slidably mounted in a support frame and is moveable by a handle located externally of the housing.

10. Apparatus as claimed in claim 1, wherein at least a portion of the housing is made from a transparent plastics material allowing the needle removal to be observed from outside of the housing.

11. Apparatus for the removal of a needle assembly having a needle hub which is screw-threadedly engaged with a syringe, said apparatus comprising a housing having an opening for insertion of the needle assembly and adjacent portion of the syringe, a socket mounted within the body in alignment with the opening, said socket having a cavity internally shaped to receive the hub and a coaxial through-bore to accommodate the needle, the socket cavity holding the hub rotationally fast relative thereto allowing the syringe unscrew from the needle assembly, and an ejector means comprising a reciprocable pin which is arranged coaxially with the through-bore and is a sliding fit therein for ejecting the unscrewed needle assembly from the socket into a collection container located within the housing, the socket being rotated by a motor to unscrew a needle hub when the syringe is held stationary relative to the housing.

* * * * *